United States Patent [19]
Kriauciunas et al.

[11] Patent Number: 4,927,427
[45] Date of Patent: May 22, 1990

[54] LITHOTRIPTOR DEVICE FOR TRAPPING AND DESTROYING CONCRETIONS

[75] Inventors: G. Vincent Kriauciunas, Westchester; Karen Vance, Palatine, both of Ill.

[73] Assignee: Northgate Research, Inc., Arlington Heights, Ill.

[21] Appl. No.: 414,396

[22] Filed: Sep. 29, 1989

[51] Int. Cl.$^5$ ............................................. A61B 17/22
[52] U.S. Cl. ................................................... 606/128
[58] Field of Search ..................... 128/24 A; 604/22; 606/127, 128

[56] References Cited
U.S. PATENT DOCUMENTS

| | | |
|---|---|---|
| 4,203,429 | 5/1980 | Vasilevsky et al. ................. 606/128 |
| 4,557,255 | 12/1985 | Goodman ............................ 606/127 |

FOREIGN PATENT DOCUMENTS

| | | | |
|---|---|---|---|
| 2747031 | 5/1979 | Fed. Rep. of Germany | ...... 606/128 |
| 2829159 | 1/1980 | Fed. Rep. of Germany | ...... 606/128 |
| 3633527 | 4/1988 | Fed. Rep. of Germany | ...... 606/128 |

Primary Examiner—Ruth S. Smith
Assistant Examiner—K. M. Pfaffle
Attorney, Agent, or Firm—Robert M. Wolters

[57] ABSTRACT

A device is provided for removal of kidney stones. The device includes a stone trapping device on the end of a flexible and axially movable wire. The wire moves through a tubing. An electrode is provided in the form of a cylinder at the outer end of the tubing. The stone is drawn into close proximity to the electrode, and electrical sparks jump between the wire and the electrode to generate a shock wave in close proximity to the stone. Stones which are small as they occur or which are reduced in size by shock wave treatment then may be withdrawn from the body in the stone trapping device.

11 Claims, 1 Drawing Sheet

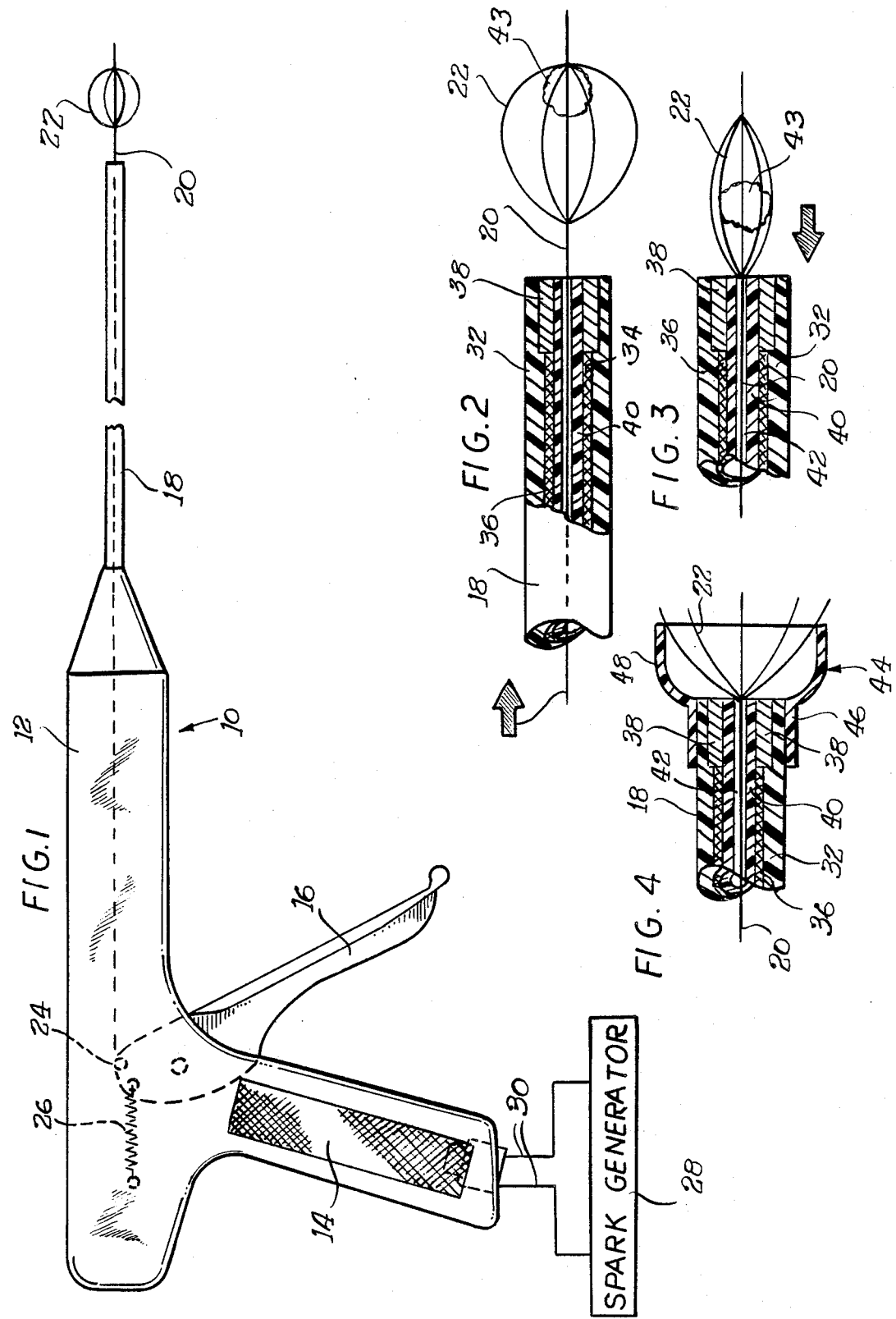

LITHOTRIPTOR DEVICE FOR TRAPPING AND DESTROYING CONCRETIONS

Kidney stones and other naturally occurring stones in the urinary bladder, gall bladder, kidneys, or ureter can be exquisitely painful, and in the past have required surgical relief. Excision or destruction of stones in the bladder and sometimes in the ureter can often be accomplished with relative ease, but surgical removal of stones from the kidney or gall bladder is a major procedure.

Surgical removal of stones from the kidney is a very serious and traumatic surgical procedure, requiring a long recuperative procedure. A large incision is made in the body. The kidney is essentially removed from the body and cut open. The stone or stones are then removed whereupon the kidney is sutured and returned to the body, with the body then being sutured. Typical recuperative periods run up to a year, and a kidney can generally be subjected to such surgery a maximum of three times. Various efforts have been made to destroy or disintegrate kidney stones so that they can be excreted with the urine.

Chemotherapy is available as a non-inavasive therapy for uric acid stones. In this therapy, the urine is alkalyzed, and the stone is dissolved over a substantial period of time. This procedure is not generally available with other types of stones. Furthermore, it requires detection of the stone before an acute phase is reached. In the gall bladder, an ether flushing procedure is sometimes used.

More recently, successful efforts have been made to fragment kidney stones with the use of ultrasound or an electro-hydraulic shock have produced by discharging a capacitor across a spark gap under water or other suitable liquid. One type of apparatus successfully used for such kidney stone and the like destruction or disintegration includes invasion of the body through the urethra or through a surgical incision, with the shock wave being generated in close proximity to the stone.

If a kidney stone or the like is not imbedded in tissue, it is likely to move when subjected to a shock wave. This requires continued monitoring of the position of the stone, and this may require excessive x-raying of the body. Heretofore, to the best of our knowledge, there has not been any mechanism for satisfactorily anchoring a stone under treatment.

Some stones are small enough that they can be captured by a cage which extends into the body to the vicinity of the stone on the end of an elongated wire or the like. This procedure is satisfactory only with relatively small stones that can be removed through a pilot tubing inserted through the urethra or through a surgical incision. This procedure is somewhat difficult and rather time consuming if there is a large number of stones or stone fragments.

OBJECTS AND SUMMARY OF THE INVENTION

In accordance with the present invention it is an object to provide an apparatus for the destruction of kidney stones and the like which includes a callapsible wire basket for trapping a stone and holding it in fixed position and cooperating with ancillary structure for generating a spark gap shock wave in the immediate vicinity of the stone.

In carrying out the foregoing and other objects of the present invention, we provide an apparatus somewhat in the shape of a handgun. An elongated flexible tubing extends therefrom and is insertable into the kidney, the ureter, or the gall bladder through a pilot tubing or scope previously inserted through a surgical incision or through the urethra, as is appropriate. The tubing includes a spark gap electrode within its outer end, and this is connected through suitable wiring to a spark gap generator exteriorly disposed relative to the apparatus. An elongated flexible wire extends through the tubing and carries at its outer end a wire cage that tends to extend into substantially spherical position when the wire is extended by pulling on a trigger forming a part of the handgun-like portion of the apparatus. The wire is retracted by a resilient spring, and the cage is partially collapsed to pull a stone trapped within the cage into proximity to the aforementioned electrode. The wire and cage serve as the second spark gap electrode, whereby a spark is generated to effect generation of a shock wave in the immediate vicinity of the stone. Successive shocks break the stone into smaller pieces, which then can be withdrawn along with the apparatus.

THE DRAWINGS

The invention best will be understood from the following description when taken in connection with the accompanying drawings wherein:

FIG. 1 is a side view showing the apparatus or device of the present invention;

FIG. 2 is a fragmentary view on an enlarged scale of the end portion of the tubing with the accompanying axially movable wire and the collapsible basket;

FIG. 3 is view similar to FIG. 2 sharing the wire and basket partially retracted; and FIG. 4 is fragmentary view similar to FIG. 2 showing a modification of the present invention.

DETAILED DISCLOSURE OF THE PREFERRED EMBODIMENTS OF THE PRESENT INVENTION

Reference first should be made to FIG. 1 wherein there is shown a device or apparatus 10 construction in accordance with the present invention and generally in the shape of a handgun, including a barrel 12, a handle or handgrip 14 and a trigger 16. A flexible tube or tubing 18 extends from the tapered front end of the barrel 12 and carries within it an axially movable flexible wire 20. The tubing is of flexible construction and will be described shortly in greater detail. A wire basket 22 is carried adjacent the outer end of the wire 20, and the opposite end of the wire is connected at anchor 24 to the top end of the trigger 16. A retracting spring 26 is connected between the upper end of the trigger, generally adjacent the anchor 24, and to a fixed anchor within the device, and tends to retract the wire 20 and basket 22. An electric spark generator 28 is connected by means of a pair of wires 30 to respective electrodes as will be described shortly hereinafter.

As best may be seen in FIG. 2, the tube 18 includes an outer insulating jacket or sheath 32 of heat shrink plastic material, having a hollow central bore 34. A copper braid 36 lines the insulating jacket or sheath 32 and is connected to the grounded one of the wires 30 from the spark generator 28. The end of the jacket 32 is provided with a counterbore in which is positioned a cylindrical electrode 38 which may be made of brass, or of tungsten for longer life. The electrode 38 is electrically connected to the copper braid 36.

A tough, flexible plastic sleeve 40 of the type generally known as TEFLON lies within the copper braid 36 and the electrode 38 and is provided with a narrow central bore 42 accommodating the wire 20.

The central wire 20 is made of stainless steel, and the basket 22 comprises a plurality of stainless steel wires welded at either end to the central wire 20, and resiliently bowed outwardly as shown in FIGS. 1 and 2. The basket can be manipulated to trap a stone 43 within it. The physician's hand then relaxes its grip on the trigger 16, and the spring 26 retracts the central wire 20 and basket 22 to a point where the basket tends to enter the central bore 42 of the TEFLON sleeve 40, thereby wedging the wires of the cage 22 into the start of the bore, reducing the outside diameter of the basket to a point where it will grip the stone 43 and hold it in close alignment with the end of the tube 18. As will be understood, an endoscope is first inserted into proximity with the stone by known means, either through a surgical incision, or through the urethra. The endoscope includes both a light source and fiber optics so that the stone can be seen when the endoscric is properly inserted. The tubing 18 of the present apparatus then is inserted through an endoscope for manipulation of the present apparatus to effect capture of a stone by the basket, as noted above. The central wire 20 and the basket 22 are electrically connected to the nongrounded one of the leads 30 from the spark generator 28. When the stone has been pulled into position adjacent the end of the tubing as heretofore described with regard to FIG. 3, electrical potential is applied by the spark generator 28 to the wires or leads 30 to cause a spark to jump along the outer end of the TEFLON sleeve 40 between the electrode 38 and the central wire 20 and/or basket 22. This portion of the present apparatus is in an electrically conductive aqueous medium, which natural body fluids such as urine, augmented, if need be, by saline solution. The sparks jumping through this aqueous medium cause vaporization of the aqueous medium in the vicinity of the spark, with a resulting shock wave which engages the closely held stone 43, and eventually breaks it into much smaller fragments. Large fragments of the stone are retained in the basket and withdrawn with the present device or apparatus, while, at least in the case of kidney stones, smaller fragments may escape from the basket, and subsequently pass out of the body with the urine.

A modification of the invention is shown in FIG. 4, wherein the parts heretofore identified are shown and identified by the same numerals as originally used. A modification comprises in the addition of a resilient plastic cap 44 at the end of the tubing 18. This cap includes a cylindrical portion 46 which grips the outer jacket or sheath 32 adjacent the end thereof, and a cup-shaped portion 48 extending axially and radially outwardly therefrom. The cap 44 helps in locating the basket 22 relative to the tubing 18, and in collapsing the basket to pull a stone into close proximity with the end of the tubing 18. It also helps to focus the shock wave on the stone, and provides protection for adjacent tissue.

The specific examples of the invention as herein shown and described will be understood as being for illustrative purposes only. Various changes will occur to those skilled in the art and will be understood as forming a part of the present invention insofar as they fall within the spirit and scope of the appended claims.

The invention is claimed as follows:

1. An electrohydraulic lithotriptor device to be used with an endoscope for trapping and destroying concretions such as kidney stones comprising:
    a base part, having a manually operable trigger,
    a flexible, insulating tubing, having one end connected to and extending from said base part and having the other end adapted to be positioned adjacent a concretion by insertion through said endoscope,
    an electrically conductive wire, extending and axially movable through and beyond said tubing and having an exposed end,
    a stone trapping device secured to said wire adjacent said exposed end and adapted to trap said concretion,
    an electrode carried by said tubing, adjacent said exposed end, said wire being retractable to pull said concretion trapped by said stone trapping device into close proximity to said other end of said tubing and to said electrode,
    means on said base part, and controlled by said trigger, for extending and retracting said wire,
    a spark generator,
    and means extending through said base part and said tubing for electrically connecting said wire and said electrode to said spark generator for causing a succession of sparks to jump between said wire and said electrode adjacent said other end of said tubing to generate a shock wave adjacent said concretion to effect destruction thereof.

2. A device as set forth in claim 1 wherein said electrode comprises a cylinder.

3. A device as set forth in claim 1 wherein said stone trapping device comprises a basket.

4. A device as set forth in claim 2 wherein said stone trapping device comprises a basket.

5. A device as set forth in claim 1 and further including a flexible metallic, braid disposed with said tubing and insulated from said wire, said braid comprising a portion of the connection between said spark generator and said electrode, and further serving as an electrical shield for said wire.

6. A device as set forth in claim 2 and further including a flexible metallic braid disposed within said tubing and insulated from said wire, said braid comprising a portion of the connection between said spark generator and said electrode, and further serving as an electrical shield for said wire.

7. A device as set forth in claim 5 and further including a plastic sleeve disposed within said braid and having an axial bore through which said wire extends, said plastic sleeve insulating said wire from said braid.

8. A device as set forth in claim 7 wherein said electrode comprises a cylinder and, said cylinders being connected to said braid.

9. A device as set forth in claim 8 wherein said stone trapping device comprises a basket.

10. A device as set forth in claim 1 and further including a cup-like insulating member extending outwardly from said other end of said tubing.

11. A device as set forth in claim 10 wherein said stone trapping device comprises a basket said basket being engagable with said cup-like device such that the basket is radially collapsed upon retraction of said wire.

* * * * *